United States Patent [19]
Martinez et al.

[11] Patent Number: 6,153,655
[45] Date of Patent: Nov. 28, 2000

[54] TERMINALLY-BRANCHED POLYMERIC LINKERS AND POLYMERIC CONJUGATES CONTAINING THE SAME

[75] Inventors: Anthony J. Martinez, Hamilton Square; Annapurna Pendri, Matawan; Richard B. Greenwald, Somerset; Yun H. Choe, Piscataway, all of N.J.

[73] Assignee: Enzon, Inc., Piscataway, N.J.

[21] Appl. No.: 09/062,305

[22] Filed: Apr. 17, 1998

[51] Int. Cl.$^7$ ...................................................... A61K 47/30
[52] U.S. Cl. ........................ 514/772.3; 514/283; 514/506; 514/513; 514/515; 514/613; 514/626; 525/54.1; 560/147; 560/155; 560/169; 560/179; 560/182
[58] Field of Search .................................. 514/772.3, 283, 514/506, 513, 515, 613, 626; 525/54.1; 560/147, 155, 169, 179, 182

[56] References Cited

U.S. PATENT DOCUMENTS

| | | | |
|---|---|---|---|
| 4,179,337 | 12/1979 | Davis et al. | 435/181 |
| 4,943,579 | 7/1990 | Vishnuvajjala et al. | 514/283 |
| 5,183,660 | 2/1993 | Ikeda et al. | 424/94.3 |
| 5,283,339 | 2/1994 | Arnold et al. | 548/104 |

(List continued on next page.)

FOREIGN PATENT DOCUMENTS

| | | |
|---|---|---|
| WO 81/01145 | 4/1981 | WIPO. |
| WO 93/24476 | 12/1993 | WIPO. |
| WO 95/10304 | 4/1995 | WIPO. |
| WO 96/23794 | 8/1996 | WIPO. |

OTHER PUBLICATIONS

Charlish, Peter. Improved Drug Targeting Polymer Therapeutics Pharmaprojects, Jan. '96, pp. 16–18.

Greenwald, R.B., Review Oncalogic, Endocrine &Metabolic Drug Delivery Systems: anticancer prodrug and their polymeric conjugates. Exp. Opin. Ther. Patents (1997) 7(6): 601–609.

Ohya, J., et al. *Bioactive and Compatible Polymers* vol. 10 Jan., 1995, 51–66.

Shearwater Polymers, Inc. catalog *Polyethylene Glycol Derivatives 1997–1998*.

(List continued on next page.)

*Primary Examiner*—Francisco Prats
*Attorney, Agent, or Firm*—Roberts & Mercanti LLP

[57] ABSTRACT

The present invention is directed to polymeric- prodrug transport forms of the formula:

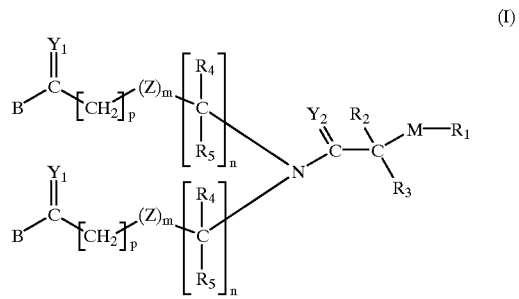

wherein:
B is a leaving group, OH, a residue of a hydroxyl-containing moiety or

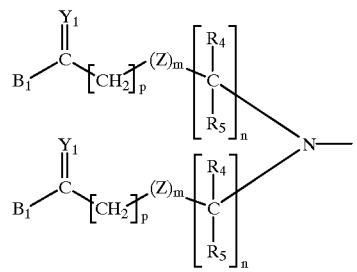

wherein
$B_1$ is a leaving group, OH or a residue of a hydroxyl-containing moiety;
$Y_{1-2}$ are independently O or S;
M is selected from either X or Q; wherein X is an electron withdrawing group and Q is a moiety containing a free electron pair positioned three to six atoms from $C(=Y_2)$; $R_{2-5}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;
(m) is zero or one;
(n) is a positive integer;
(p) is zero or a positive integer;
Z is an electron withdrawing group; and
$R_1$ is a polymeric residue which is optionally capped with a moiety of the Formula (v)

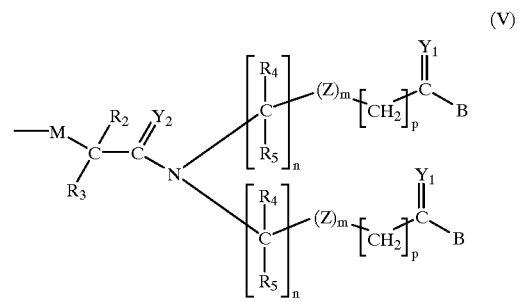

17 Claims, 5 Drawing Sheets

U.S. PATENT DOCUMENTS

| | | | |
|---|---|---|---|
| 5,433,886 | 7/1995 | Sherbondy et al. | 252/180 |
| 5,454,954 | 10/1995 | Alfano et al. | 210/700 |
| 5,489,589 | 2/1996 | Wittman et al. | 514/232.8 |
| 5,498,729 | 3/1996 | Domb | 548/500 |
| 5,547,981 | 8/1996 | Greenwald et al. | 514/449 |
| 5,569,720 | 10/1996 | Mongelli et al. | 525/329.4 |
| 5,583,206 | 12/1996 | Snow et al. | 534/16 |
| 5,614,549 | 3/1997 | Greenwald et al. | 514/449 |
| 5,622,986 | 4/1997 | Greenwald et al. | 514/449 |
| 5,643,575 | 7/1997 | Martinez et al. | 424/194.1 |
| 5,646,159 | 7/1997 | Wall et al. | 514/279 |
| 5,679,852 | 10/1997 | Platzek et al. | 564/138 |
| 5,693,310 | 12/1997 | Gries et al. | 424/9.365 |
| 6,020,373 | 2/2000 | Schellenberg et al. | 514/547 |

OTHER PUBLICATIONS

Williams, Matthew A., and Henry Rapoport, Synthesis of Enantiomerically Pure Diethyletriaminepentaacetic Acid Analogues J. Org. Chem, 58, 1151–1158 (1993).

Zalipsky, S., C. Gilon and A. Zilkha, Attachment of Drugs to Polyethylene Glycols Eur. Polym. J vol. 19, No. 12, pp. 1177–1183, 1983.

Weiner, Ben–Zoin and Albert Zilkha, Polyethylene Glycol Derivatives of Procaine J. Med. Chem (1973) vol. 16, No. 5, 573–574.

Shearwater Polymers, Inc. Quarterly Newsletter Mar. 1998.

Greenwald, R.B., et al. Highly Waater Soluble Taxol Derviatives 2'–Polythleneglycol Esters As Potential Prodrugs, *Bioorganic & Medical Chemistry Letters,* vol. 4 No. 20, pp. 2465–2470, 1994.

Ouchi, T., et al. Synthesis And Antitumor Activity of Poly–(Ethylene Glycol)s Linked to 5–Fluorouracil Via A Urethane or Urea Bond. Drug Design & Discovery, 1992, vol. 9, pp. 93–105.

Ueda, Y., et al. Synthesis and Antiumor Evaluation of 2–Oxcarbonylpaclitaxels Bioorganic & Medical Chemistry Letters, vol. 4, No. 15. pp. 1861–1864, (1994).

Duncan, Ruth. Drug–Polmer Conjugates: Potential for Improved Chemotherapy Anti–Cancer Drugs 3. pp. 175–210, 1992.

Caliceti, P., Preperation and Properties of Monmethoxy Poly (Etholylene Glycol) Doxorubicin Conjug Linked by an Amino Acid or a Peptide As Spacer. IL Farmaco, 48(7), 919–932: 1993.

Harris, J. Milton. Laboratory Synthesis of Polyethylene Glycol Derivatives. JMS–Rev. Macromol. Chem. Phys., C25(3), 325–373 (1985).

Ulbrich, Karl. Poly(ethylene glycols)s containing enzymatically degradable bonds. Makromol. Chem. 187, 1131–1144 (1986).

Cerny, L. C., et al. A Potential Blood Substitued From A Tetronic Polyol And A Modifid Hemoglob Biomat, Art. Cells & Immob. Biotech., 20(1), 71–93 (1992).

Bogdanov, Alexi A. Jr., et al Long–Circulating Blood Pool Imaging Agents Advanced Drug Delivery Reviews 16 (1995) 335–348.

FIG. 1 METHOD A

TERMINALLY-BRANCHED POLYMERIC LINKERS AND POLYMERIC CONJUGATES CONTAINING THE SAME

TECHNICAL FIELD

The present invention relates to new types of terminally-activated polymeric materials which are useful in forming long-acting conjugates of bioactive materials. In particular, the invention relates to polymeric-based conjugates having increased therapeutic payloads and methods of preparing the same.

BACKGROUND OF THE INVENTION

Over the years, several methods of administering biologically-effective materials to mammals have been proposed. Many medicinal agents are available as water-soluble salts and can be included in pharmaceutical formulations relatively easily. Problems arise when the desired medicinal agent is either insoluble in aqueous fluids or is rapidly degraded in vivo. Alkaloids are often especially difficult to solubilize.

One way to solubilize medicinal agents is to include them as part of a soluble prodrug. Prodrugs include chemical derivatives of a biologically-active parent compound which, upon administration, eventually liberate the parent compound in vivo. Prodrugs allow the artisan to modify the onset and/or duration of action of an agent in vivo and can modify the transportation, distribution or solubility of a drug in the body. Furthermore, prodrug formulations often reduce the toxicity and/or otherwise overcome difficulties encountered when administering pharmaceutical preparations. Typical examples of prodrugs include organic phosphates or esters of alcohols or thioalcohols. See *Remington's Pharmaceutical Sciences,* 16th Ed., A. Osol, Ed. (1980), the disclosure of which is incorporated by reference herein.

Prodrugs are often biologically inert or substantially inactive forms of the parent or active compound. The rate of release of the active drug, i.e. the rate of hydrolysis, is influenced by several factors but especially by the type of bond joining the parent drug to the modifier. Care must be taken to avoid preparing prodrugs which are eliminated through the kidney or reticular endothelial system, etc. before a sufficient amount of hydrolysis of the parent compound occurs.

Incorporating a polymer as part of a prodrug system has been suggested to increase the circulating life of a drug. However, it has been determined that when only one or two polymers of less than about 10,000 daltons each are conjugated to certain biologically active substances such as alkaloid compounds, the resulting conjugates are rapidly eliminated in vivo, especially if a somewhat hydrolysis-resistant linkage is used. In fact, such conjugates are so rapidly cleared from the body that even if a hydrolysis-prone ester linkage is used, not enough of the parent molecule is regenerated in vivo to be therapeutic.

Camptothecin and related biologically active analogs are often poorly water soluble and are examples of substances which would benefit from PEG prodrug technology. A brief overview of some previous work in the field is presented below.

Ohya, et al., J. *Bioactive and Compatible Polymers* Vol. 10 January, 1995, 51–66, disclose doxorubicin-PEG conjugates which are prepared by linking the two substituents via various linkages including esters. The molecular weight of the PEG used, however, is only about 5,000 at most. Thus, the in vivo benefits are not fully realized because the conjugates are substantially excreted prior to sufficient linkage hydrolysis.

U.S. Pat. No. 4,943,579 discloses certain simple 20(S)-camptothecin amino acid esters in their salt forms as water soluble prodrugs. The reference does not, however, disclose using an amino acid as part of a linkage which would attach the alkaloid to a relatively high molecular weight polymer in order to form a prodrug. As evidenced by the data provided in Table 2 of the '579 patent, hydrolysis is rapid. Consequently, at physiologic pH, the insoluble base is rapidly generated after injection, binds to proteins and is quickly eliminated from the body before a therapeutic effect can be achieved. A related effort was directed to developing a water-soluble camptothecin sodium salt. Unfortunately, the water-soluble sodium salt of camptothecin remained too toxic for clinical application (Gottlieb et al,. 1970 *Cancer Chemother*, Rep. 54, 461; Moertel et al,. 1972 ibid, 56, 95; Gottlieb et al., 1972 ibid, 56, 103).

As an outgrowth of the work in the prodrug field, it has been thought that it would be beneficial in some situations to increase the payload of the polymeric transport form. This technique was offered as an alternative to the many approaches in which a single molecule of a therapeutic moiety containing a substitutable hydroxyl moiety is attached to a terminal group found on the polymer. For example, commonly-assigned PCT publication WO96/23794 describes bis-conjugates in which one equivalent of the hydroxyl-containing drug is attached to each terminal of the polymer. In spite of this advance, techniques which would further increase the payload of the polymer have been sought.

Thus, there continues to be a need to provide additional technologies for forming prodrugs of therapeutic moieties such as camptothecin and related analogs. The present invention addresses this need.

SUMMARY OF THE INVENTION

In one aspect of the invention, compounds of Formula (I) are provided:

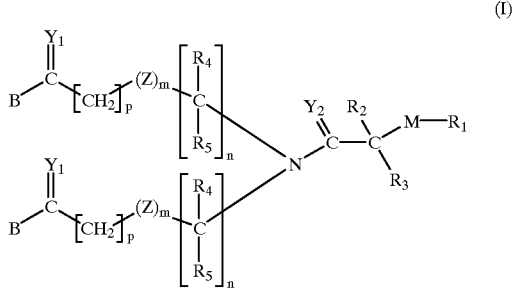

(I)

wherein:

B is a leaving group, OH, a residue of a hydroxyl-containing moiety or

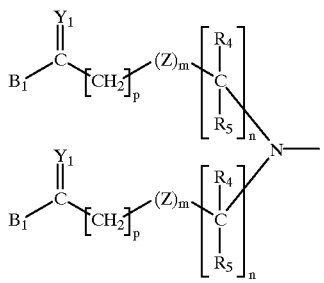
(II)

wherein
- $B_1$ is a leaving group, OH or a residue of a hydroxyl-containing moiety;
- $Y_{1-2}$ are independently O or S;
- M is selected from either X or Q; wherein X is an electron withdrawing group and Q is a moiety containing a free electron pair positioned three to six atoms from $C(=Y_2)$;
- $R_{2-5}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;
- (m) is zero or one;
- (n) is a positive integer;
- (p) is zero or a positive integer;
- Z is an electron withdrawing group; and
- $R_1$ is a polymeric residue such as a water-soluble polyalkylene oxide, preferably having a molecular weight $\geq$ about 20,000 Daltons and preferably including a capping group which provides bis compounds of the formula (I')

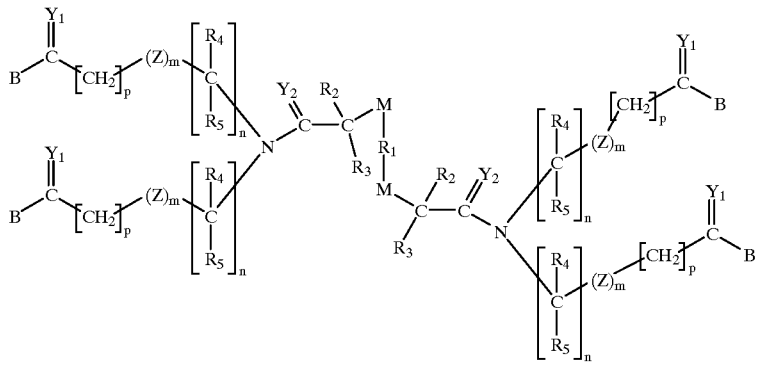

where all variables are as previously defined.

In another aspect of the invention there are provided compounds of the formula:

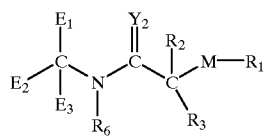
(III)

wherein
- $R_{1-3}$, M and $Y_2$ are as defined above with respect to Formula (I) and $R_6$ is one of hydrogen (preferred), $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, branched alkyls, aryls, substituted aryls, $C_{1-6}$ alkyl aralkyls, heteroalkyls, substituted heteroalkyls or substituted $C_{1-6}$ alkyls such as carboxyalkyls, aminoalkyls, dialkylaminos, hydroxyalkyls or mercaptoalkyls, etc.; and
- $E_{1-3}$ are independently H or

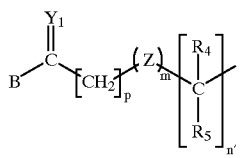

wherein:

B, m, p, $R_4$, $R_5$, $Y_1$ and Z are defined above with respect to Formula (I), n' is zero or n except that $E_{1-3}$ are not all simultaneously H and (m) is not zero when M is oxygen.

Examples of hydroxyl-containing compound residues (B) for which one or more of improved aqueous solubility, decreased antigenicity, prodrug and/or controlled release delivery is desired include chemotherapeutic compound residues such as anti-fungal compounds, including triazoles, echinocandins, pneumocandins, etc, anti-cancer compounds such as camptothecin, paclitaxel, etoposide, anti-cancer platinum compounds containing OH groups, floxuridine or podophyllotoxin. In still further embodiments, other oncolytic agents, non-oncolytic agents such as anti-inflammatory agents, including steroidal compounds, as well as therapeutic low molecular weight peptides such as insulin are also contemplated. Alternatively, B can be a leaving group such as N-hydroxy-benzotriazolyl, N-hydroxyphthalimidyl, halogen, p-nitrophenoxy, imidazolyl, N-hydroxysuccinimidyl, thiazolidyl thione, or other activating groups.

For purposes of the present invention, the term "residue" shall be understood to mean that portion of a biologically active compound which remains after it has undergone a substitution reaction in which the prodrug carrier portion has been attached.

For purposes of the present invention, the term "alkyl" shall be understood to include straight, branched, substituted $C_{1-12}$ alkyls, including alkoxy, $C_{3-8}$ cycloalkyls or substituted cycloalkyls, etc.

The term "sufficient amounts" for purposes of the present invention shall mean an amount which achieves a therapeutic effect as such effect is understood by those of ordinary skill in the art.

In some preferred embodiments of the invention, $R_1$ includes both an alpha and an omega linking group so that up to four or more equivalents of a biologically active ingredient or drug, designated herein as B and/or $B_1$, can be delivered. Each B (or $B_1$) is attached via a hydrolyzable ester linkage which attaches to the polymer residue terminus.

One of the chief advantages of the compounds of the present invention is that the prodrugs have a higher payload per unit of polymer than previous techniques, especially when the bis- embodiments are used. Another advantage is that the linkers achieve a proper balance between the rate of parent drug-polymer linkage hydrolysis and the rate of clearance of prodrug from the body. The linkages between the polymer and the parent compounds, also referred to herein as biologically-active nucleophiles, hydrolyze at a rate which allows a sufficient amount of the parent molecules to be released in vivo before clearance of the prodrug from the plasma or body.

The high payload polymeric conjugates of the present invention are thus unique delivery systems which can contain up to four or a greater number of molecules of a drug.

Methods of making and using the compounds and conjugates described herein are also provided.

DETAILED DESCRIPTION OF THE INVENTION

A. The Prodrugs

Figure 1:
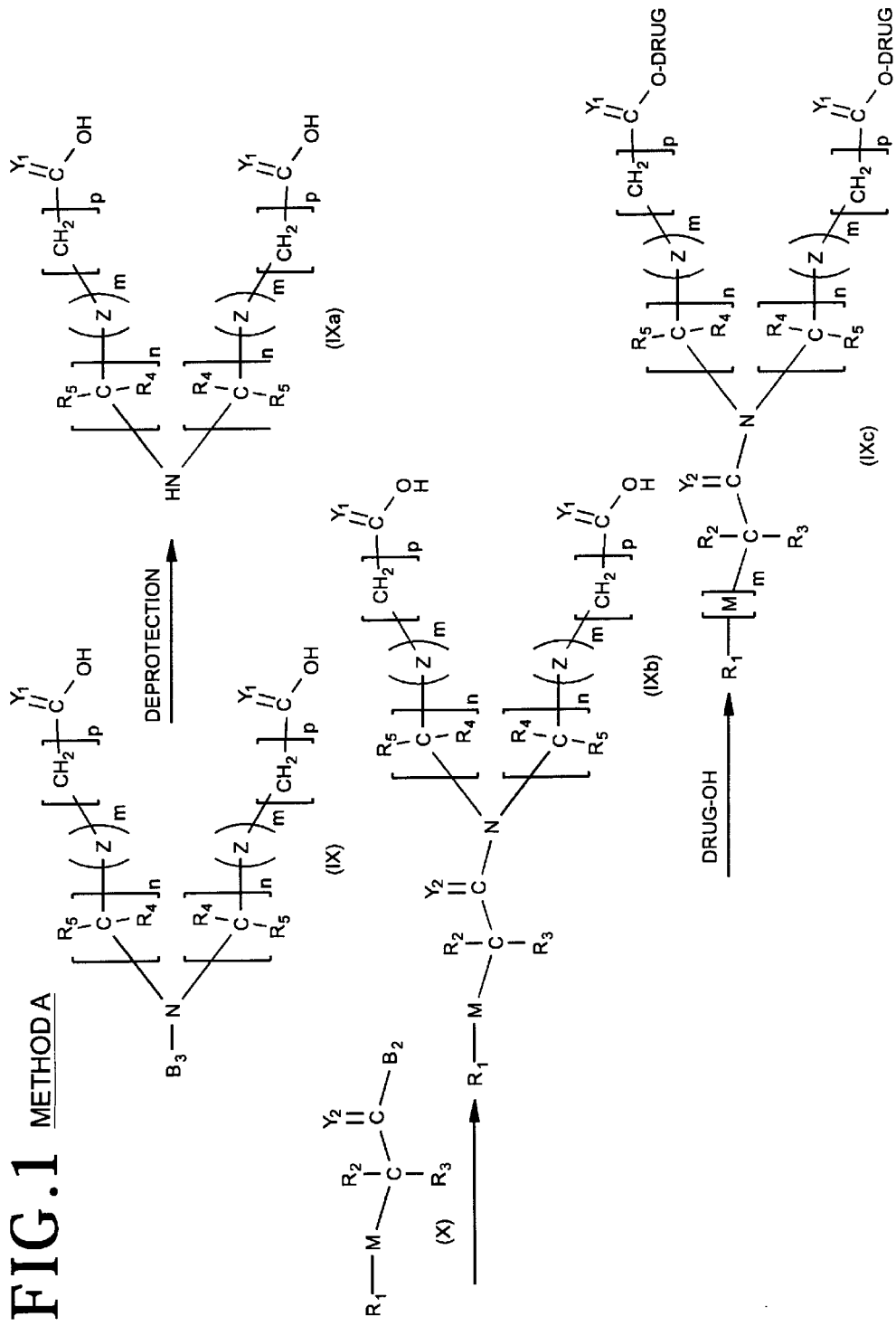
FIGS. 1–2 schematically illustrate methods of forming compounds of the present invention.

In one preferred embodiment of the invention, the prodrug compositions of the invention comprise the formula set forth below:

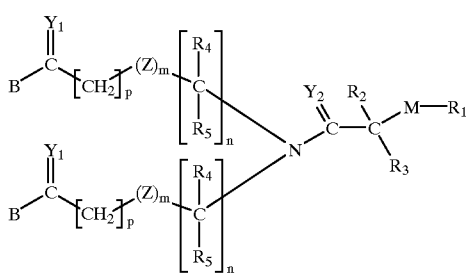

(I)

wherein

B is a leaving group, OH, a residue of a hydroxyl-containing moiety or

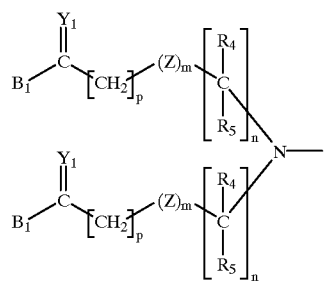

(II)

wherein $B_1$ a leaving group, OH or a residue of a hydroxyl-containing moiety;

$Y_{1-2}$ are independently O or S;

M is selected from either X or Q; wherein X is an electron withdrawing group and Q is a moiety containing a free electron pair positioned three to six atoms from $C(=Y_2)$;

$R_{2-5}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;

(m) is zero or one;

(n) is a positive integer;

(p) is zero or a positive integer;

Z is an electron withdrawing group; and $R_1$ is a polymeric residue.

Preferably, the polymer residue portion, designated $R_1$ herein, is further substituted with a terminal capping moiety (A) which is distal to the linker portion containing the branched amine. A non-limiting list of suitable capping groups includes hydrogen, $CO_2H$, $C_{1-6}$ alkyl moieties, biologically active and inactive moieties, dialkyl acyl urea alkyls, and moieties of Formula (V):

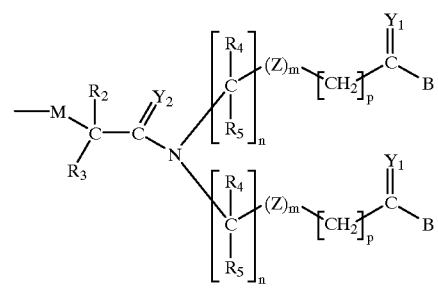

wherein

B, M, $R_{2-5}$, $Y_{1-2}$, Z, (m), (n) and (p) are as defined above.

Within Formula (I), Y and Y' are preferably oxygen, $R_{2-5}$ are preferably H, (n) is 1 or 2 and (p) is 1.

In those aspects of this embodiment where bis-substituted polymeric residues are desired, the polymeric transport systems of the invention are of the Formula (I'), shown below.

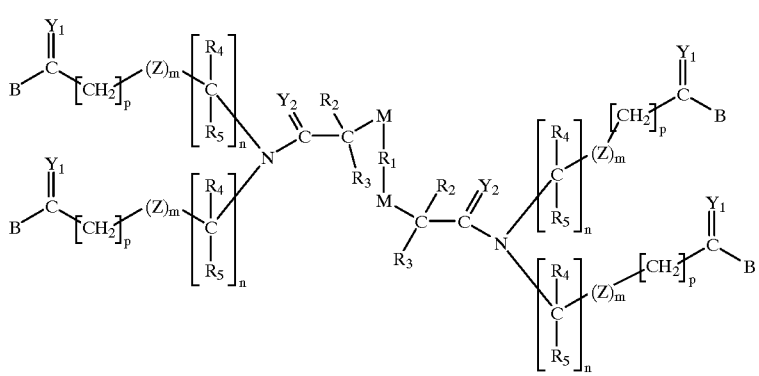
(I')

In another embodiment, there are provided compounds of Formula (III)

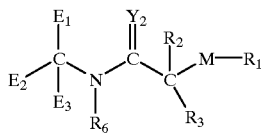
(III)

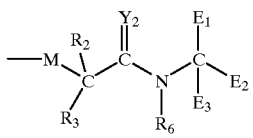
(VI)

wherein $R_{1-3}$, M and $Y_2$ are as defined above with respect to Formula (I) and $R_6$ is one of hydrogen (preferred), $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, branched alkyls, aryls, substituted aryls, $C_{1-6}$ alkyl aralkyls, heteroalkyls, substituted heteroalkyls or substituted $C_{1-6}$ alkyls such as carboxyalkyls, aminoalkyls, dialkylaminos, hydroxyalkyls or mercaptoalkyls, etc.; and $E_{1-3}$ are independently H or

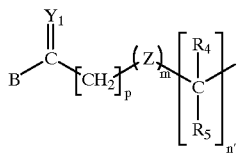

wherein:

B, (m), p, $R_4$, $R_5$, $Y_1$ and Z are defined above with respect to Formula (I), (n') is zero or (n) except that $E_{1-3}$ are not all simultaneously H and (m) is not zero when M is oxygen.

In this aspect of the invention, the capping groups suitable for $R_1$ include, without limitation, hydrogen, $CO_2H$, $C_{1-6}$ alkyl moieties, biologically active and inactive moieties, dialkyl acyl urea alkyls, and moieties of Formula (VI):

wherein all variables are the same as that set forth above; thereby forming polymeric transport systems of the Formula (VIII):

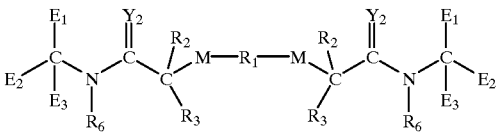
(VIII)

B. The Prodrug Linkage

1. The Electron Withdrawing Groups X and Z

Within the Formula (I), X and Z are variables which represent electron withdrawing groups. In particular, X and Z can be independently selected from moieties such as O, S, SO, $SO_2$, and $NR_{6a}$ where $R_{6a}$ is one of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls, branched alkyls, aryls, substituted aryls, $C_{1-6}$ alkyl aralkyls, heteroalkyls, substituted heteroalkyls or substituted $C_{1-6}$ alkyls such as carboxyalkyls, aminoalkyls, dialkylaminos, hydroxyalkyls or mercaptoalkyls, to name but a few. Preferably, X is either O or $NR_{6a}$ and $R_{6a}$ is preferably H. For purposes of the present invention, X is preferably a moiety which gives a substituted acetic acid with a pKa of less than about 4.0 upon hydrolysis of the prodrug ester. The moieties selected for X within the formula promote relatively rapid hydrolysis because of the low pKa of the resulting substituted acetic acid. As pointed out above with regard to (M), it will be understood by the ordinary skilled artisan, that X is a terminal heteroatom moiety of the polymeric residue ($R_1$). In preferred embodiments, when X is oxygen, the oxygen is provided as the terminal portion of the PEG polymer. The terminal oxygen can be substituted to provide the other X moieties described herein using techniques apparent to those of ordinary skill without undue experimentation.

2. Q Portion of the Linker

When M is Q, the polymer, $R_1$, is preferably attached to Q via a heteroatom such as oxygen. Q is a moiety containing a free electron pair positioned three to six atoms from the $C(=Y_2)$ moiety. In a preferred embodiment, the free electron pair is five atoms from this oxygen. Q can be selected from the non-limiting list of cycloalkyls, aryls, aralkyl groups substituted with O, S or $NR_7$ where $R_7$ is one of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls; —$CH_2$—C(=O)—NH—, and ortho-substituted phenyls such as

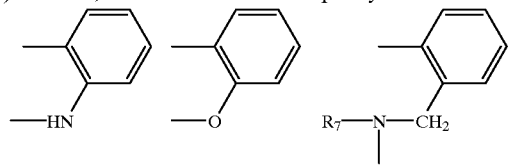

Preferably, $R_7$ is H, a $C_{1-6}$ alkyl or substituted $C_{1-6}$ alkyl. The free electron pair can be anywhere along the Q moiety as long as the defined spacing between the free electron pair and the oxygen is maintained. In these embodiments, $R_1$ is attached to Q via $NR_7$, O, or S. Thus, Q assists hydrolysis of the prodrug linkage by anchimeric assistance because the free electron pair moiety can generate a three- to six-membered, but preferably five-membered, ring by-product upon hydrolysis of the preferably ester linkage.

3. Hydrolysis and Parent Drug Regeneration

The prodrug compounds of the present invention are designed so that in plasma the $T_{1/2}$ circulation is greater than the $T_{1/2}$ hydrolysis, which in turn is greater than the $T_{1/2}$ for elimination, i.e.

$T_{1/2}$ circulation > $T_{1/2}$ hydrolysis > $T_{1/2}$ elimination.

The prior art had several shortcomings associated with its approach to providing polymer-based prodrugs. For example, in some cases, the molecular weight of the polymer was insufficient, i.e. 10,000 Daltons or less, regardless of the linkage used to attach the parent drug to the polymer. In other cases, a polymer of sufficient molecular weight was proposed but the linkage was not designed to allow sufficient in vivo hydrolysis and release of the parent molecule. The compounds of the present invention overcome these shortcomings by including not only polymers of sufficient weight but also linkages which meet the criteria discussed above.

The linkages included in the compounds of the present invention have a $T_{1/2}$ hydrolysis in the plasma of the mammal being treated which is long enough to allow the parent compounds to be released prior to elimination. Some preferred compounds of the present invention have plasma $T_{1/2}$ hydrolysis rates ranging from about 30 minutes to about 12 hours. Preferably, the compositions have a plasma $T_{1/2}$ hydrolysis ranging from about 1 to about 8 hours and most preferably from about 2.5 to about 5.5 hours. While Applicants are not bound by theory, in those aspects of the invention where prodrugs are formed, regeneration of sufficient amounts of the parent compound during the time the prodrug remains in circulation is believed to be a key to providing an effective prodrug compositions.

C. Substantially Non-Antigenic Polymers

As stated above, $R_1$ is a polymeric residue which is preferably substantially non-antigenic. Suitable examples of such polymers include polyalkylene oxides such as polyethylene glycols. The general formula for PEG and its derivatives, i.e.

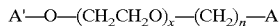

where (x) represents the degree of polymerization (i.e. 10–2,300) or number of repeating units in the polymer chain and is dependent on the molecular weight of the polymer, (n) is zero or a positive integer, (A) is a capping group as defined herein, i.e. an —H, amino, carboxy, halo, $C_{1-6}$ alkyl or other activating group and (A') is the same as (A) or another (A) moiety. It will be understood by those of ordinary skill that for purposes of the present invention at least one and preferably both capping groups are capable of undergoing a substitution reaction which allows the polymer to be converted into a residue which is part of the compounds defined by the formulae herein.

Also useful are polypropylene glycols, branched PEG derivatives such as those described in commonly-assigned U.S. Pat. No. 5,643,575, "star-PEG's" and multi-armed PEG's such as those described in Shearwater Polymers, Inc. catalog "Polyethylene Glycol Derivatives 1997–1998"; the disclosure of each is incorporated herein by reference.

Bis-activated or functionalized polymers e.g. PEG are preferred for the compounds of the present invention. Polymeric residues based on mono-activated, $C_{1-4}$ alkyl-terminated PAO's such as mono-methyl-terminated polyethylene glycols (mPEG's) can alternatively be used, if desired.

In order to provide the desired hydrolyzable linkage, di-acid activated polymers such as PEG acids or PEG diacids can be used as well as di-PEG amines. Suitable PAO acids can be synthesized by first converting mPEG-OH to an ethyl ester followed by saponification. See also Gehrhardt, H., et al. Polymer Bulletin 18:487 (1987) and Veronese, F. M., et al., J. Controlled Release 10; 145 (1989). Alternatively, the PAO-acid can be synthesized by converting mPEG-OH into a t-butyl ester followed by acid cleavage. See, for example, commonly assigned U.S. Pat. No. 5,605,976. The disclosures of each of the foregoing are incorporated by reference herein.

Although PAO's and PEG's can vary substantially in molecular weight, polymers ranging from about 2,000 to about 100,000 are usually selected for the purposes of the present invention. Molecular weights of from about 5,000 to about 50,000 are preferred and 20,000 to about 40,000 are particularly preferred. The molecular weight of the polymer selected for inclusion in the prodrug must be sufficient so as to provide sufficient circulation of the prodrug" before hydrolysis of the linker. Within the ranges provided above, polymers having molecular weight ranges of at least 20,000 are preferred for chemotherapeutic and organic moieties.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

As an alternative to PAO-based polymers, effectively non-antigenic materials such as dextran, polyvinyl alcohols, carbohydrate-based polymers, hydroxypropylmethacrylamide (HPMA), and copolymers thereof etc. and the like can be used if the same type of activation is employed as described herein for PAO's such as PEG. Those of ordinary skill in the art will realize that the foregoing list is merely illustrative and that all polymeric materials having the qualities described herein are contemplated. For purposes of the present invention, "effectively non-antigenic" means all polymeric materials understood in the art as being nontoxic and not eliciting an appreciable immune response in mammals.

It will be clear from the foregoing that other polyalkylene oxide derivatives of the foregoing, such as the polypropylene glycol acids, etc., as well as other bifunctional linking groups are also contemplated.

D. Prodrug Candidates

1. Camptothecin and Related Topoisomerase I Inhibitors

Camptothecin is a water-insoluble cytotoxic alkaloid produced by *Camptotheca accuminata* trees indigenous to China and *nothapodytes foetida* trees indigenous to India. Camptothecin and related compounds and analogs are also known to be potential anticancer or antitumor agents and have been shown to exhibit these activities in vitro and in vivo. Camptothecin and related compounds are also candidates for conversion to the prodrugs of the present invention. Camptothecin and certain related analogues share the structure:

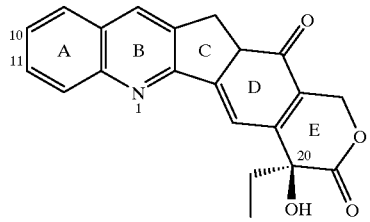

From this core structure, several known analogs have been prepared. For example, the A ring in either or both of the 10- and 11-positions can be substituted with an OH. The A ring can also be substituted in the 9-position with a straight or branched $C_{1-30}$ alkyl or $C_{1-17}$ alkoxy, optionally linked to the ring by a heteroatom i.e.—O or S. The B ring can be substituted in the 7-position with a straight or branched $C_{1-30}$ alkyl or substituted alkyl-, $C_{5-8}$ cycloakyl, $C_{1-30}$ alkoxy, phenyl alkyl, etc., alkyl carbamate, alkyl carbazides, phenyl hydrazine derivatives, amino-, aminoalkyl-, aralkyl, etc. Other substitutions are possible in the C, D and E rings. See, for example, U.S. Pat. Nos. 5,004,758; 4,943,579; Re 32,518, the contents of which are incorporated herein by reference. Such derivatives can be made using known synthetic techniques without undue experimentation. Preferred camptothecin derivatives for use herein include those which include a 20—OH or another OH moiety which is capable of reacting directly with activated forms of the polymer transport systems described herein or to the linking moiety intermediates, e.g. iminodiacetic acid, etc., which are then attached to a polymer such as PEG. Reference to camptothecin analogs herein has been made for purposes of illustration and not limitation.

2. Taxanes and Paclitaxel Derivatives

One class of compounds included in the prodrug compositions of the present invention is taxanes. For purposes of the present invention, the term "taxane" includes all compounds within the taxane family of terpenes. Thus, taxol (paclitaxel), 3'-substituted tert-butoxy-carbonyl-amine derivatives (taxoteres) and the like as well as other analogs which are readily synthesized using standard organic techniques or are available from commercial sources such as Sigma Chemical of St. Louis, Mo. are within the scope of the present invention. Representative taxanes are shown below.

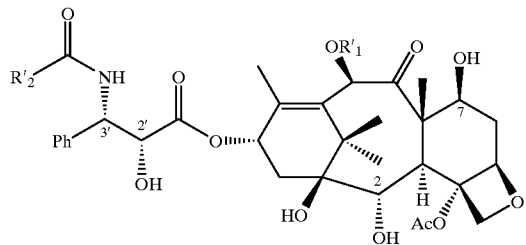

Paclitaxel: $R'_1=C_6H_5$; $R'_2=CH_3CO$; Taxotere: $R'_1=(CH_3)_3CO$; $R'_2=H$

These derivatives have been found to be effective anti-cancer agents. Numerous studies indicate that the agents have activity against several malignancies. To date, their use has been severely limited by, among other things, their short supply, poor water solubility and hypersensitivity. It is to be understood that other taxanes including the 7-aryl-carbamates and 7-carbazates disclosed in commonly assigned U.S. Pat. Nos. 5,622,986 and 5,547,981 can also be included in the prodrugs of the present invention. The contents of the foregoing U.S. patents are incorporated herein by reference. The only limitation on the taxane is that it must be capable of undergoing a hydroxyl based substitution reaction such as at the 2' position. Paclitaxel, however, is a preferred taxane.

3. Additional Biologically-Active Moieties

In addition to the foregoing molecules, the prodrug formulations of the present invention can be prepared using many other compounds. For example, biologically-active compounds such as bis-PEG esters derived from compounds such as gemcitabine:

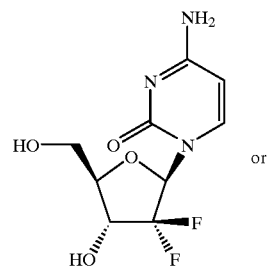

podophyllotoxin:

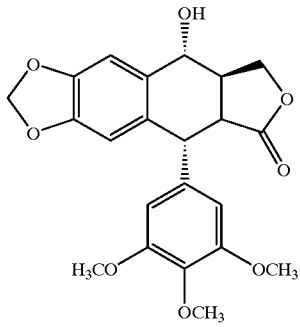

triazole-based antifungal agents such as fluconazole:

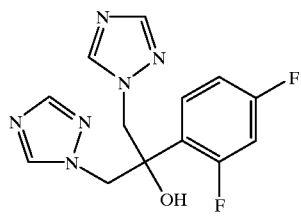

or ciclopirox:

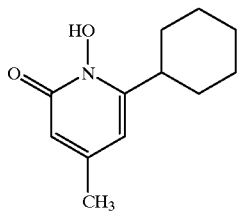

The parent compounds selected for prodrug forms need not be substantially water-insoluble, although the polymer-based prodrugs of the present invention are especially well suited for delivering such water-insoluble compounds. Other useful parent compounds include, for example, certain low molecular weight biologically active proteins, enzymes and peptides, including peptido glycans, as well as other anti-tumor agents; cardiovascular agents such as forskolin; anti-neoplastics such as combretastatin, vinblastine, doxorubicin, AraC, maytansine, etc.; anti-infectives such as vancomycin, erythromycin, etc.; anti-fungals such as nystatin, amphoteracin B, triazoles, papulocandins, pneumocandins, echinocandins, polyoxins, nikkomycins, pradimicins, benanomicins, etc. see, "Antibiotics That Inhibit Fungal Cell Wall Development" *Annu. Rev. Microbiol.* 1994, 48:471–97, the contents of which are incorporated herein by reference; anti-anxiety agents, gastrointestinal agents, central nervous system-activating agents, analgesics, fertility or contraceptive agents, anti-inflammatory agents, steroidal agents, anti-urecemic agents, cardiovascular agents, vasodilating agents, vasoconstricting agents and the like.

The foregoing is illustrative of the biologically active moieties which are suitable for the prodrugs of the present invention. It is to be understood that those biologically active materials not specifically mentioned but having suitable ester-forming groups, i.e. hydroxyl moieties, are also intended and are within the scope of the present invention. It is also to be understood that the prodrug conjugates of the present invention may also include minor amounts of compounds containing not only one equivalent of drug and polymer but also a moiety which does not effect bioactivity in vivo. For example, it has been found that in some instances, in spite of reacting diacids with drug molecules having a single linkage point, the reaction conditions do not provide quantitative amounts of prodrugs with two equivalents of drug per polymer. By-products of the reactants can sometimes be formed such as acyl ureas if carbodiimides are used.

The only limitation on the types of molecules suitable for inclusion herein is that there is at least one position on which the linkage can be attached, so that after prodrug administration, the prodrug can regenerate sufficient quantities of the parent compound in vivo.

E. Synthesis Of The Polymeric Prodrug Transport System

Figure 2:
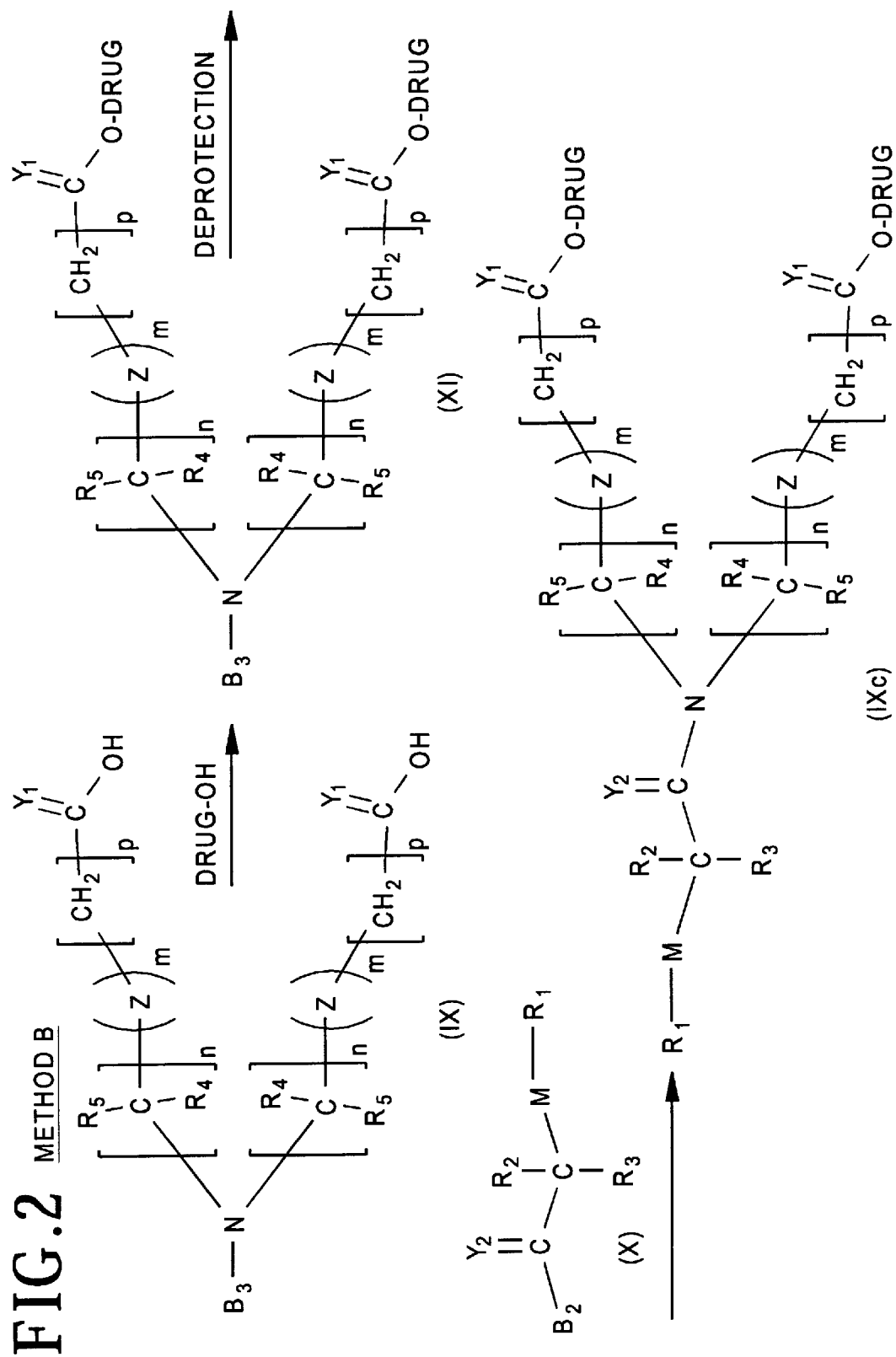
Figure 3:
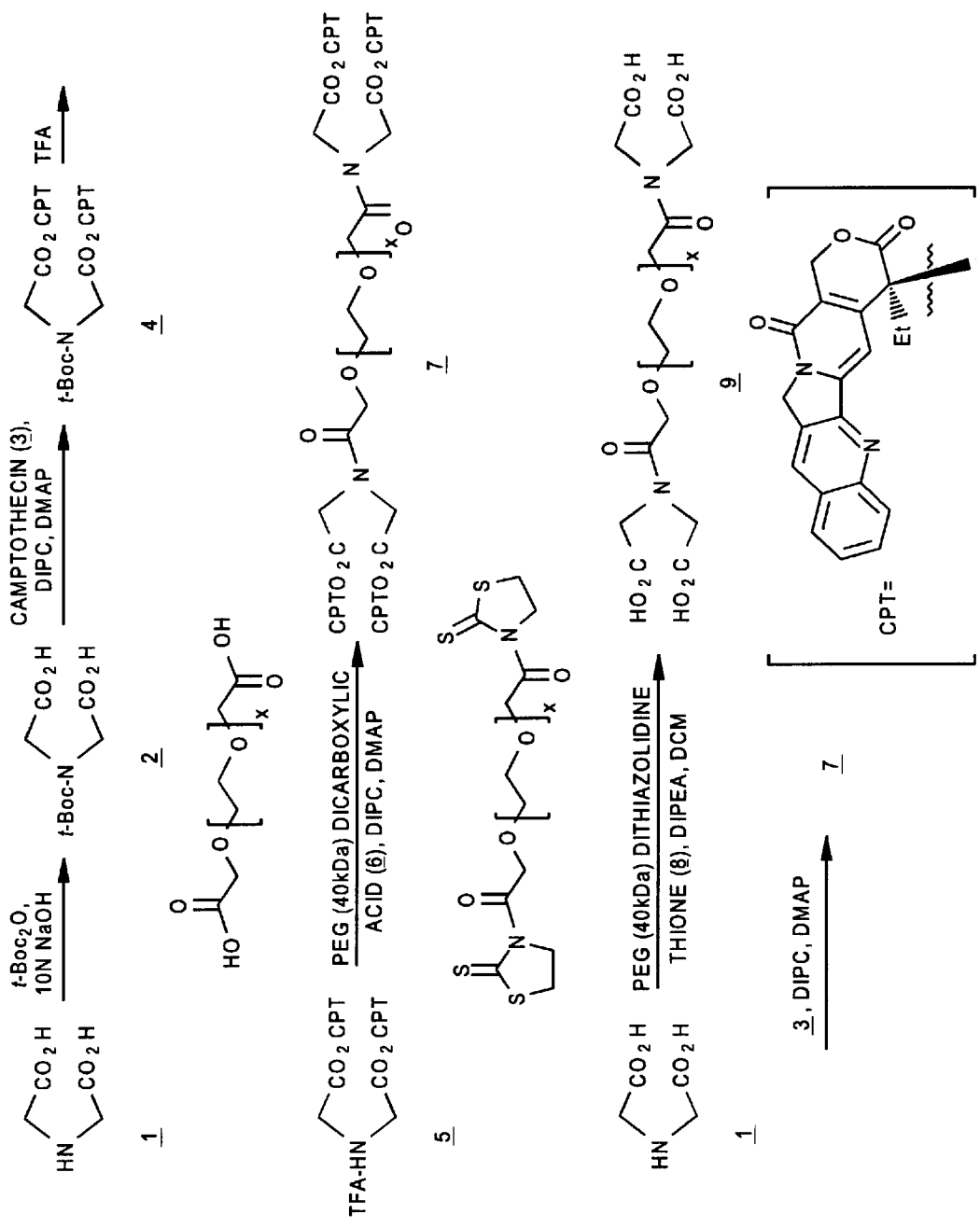
FIGS. 3–5 schematically illustrate compounds synthesized in the Examples.
Figure 4:
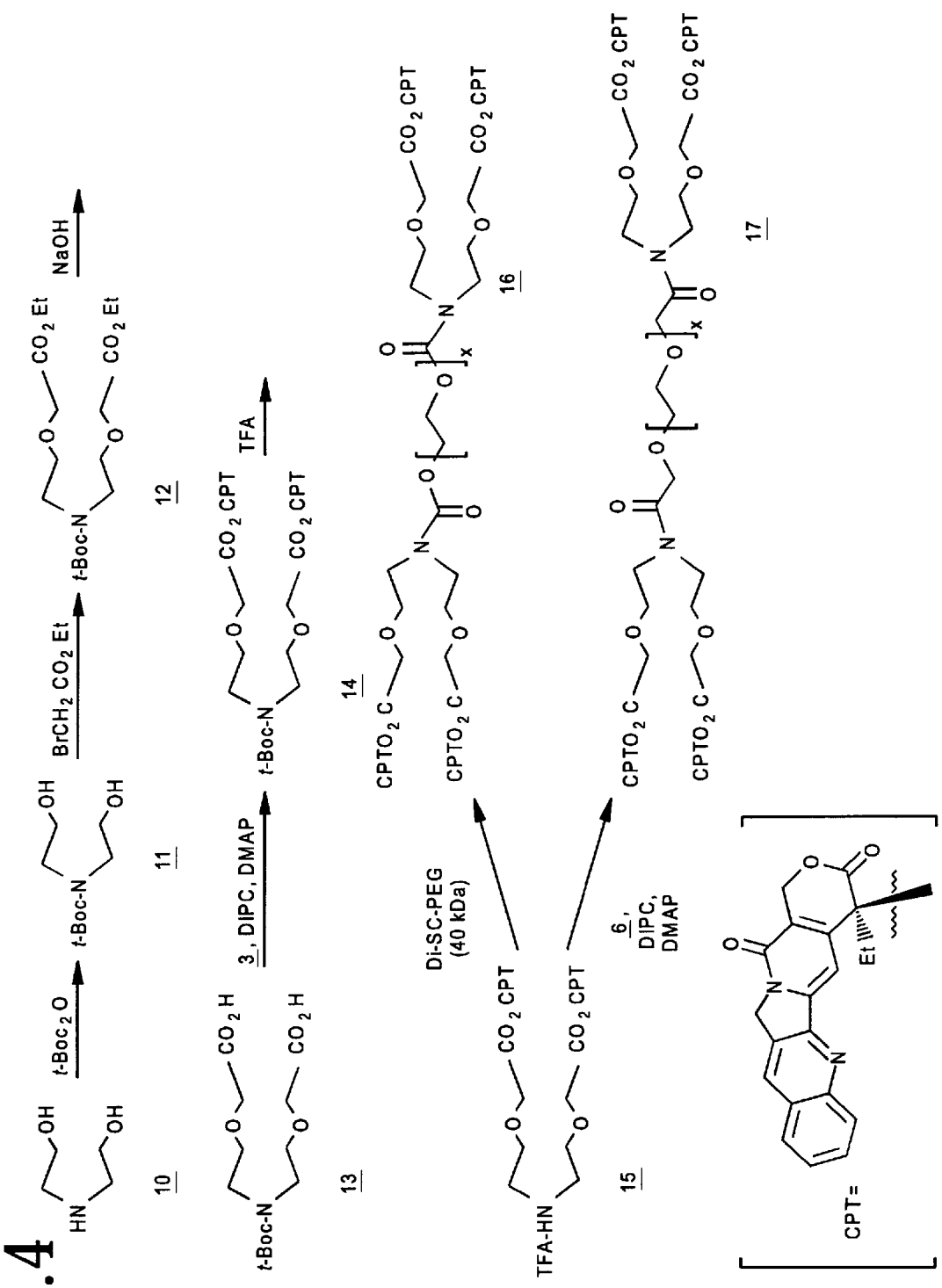
Figure 5:
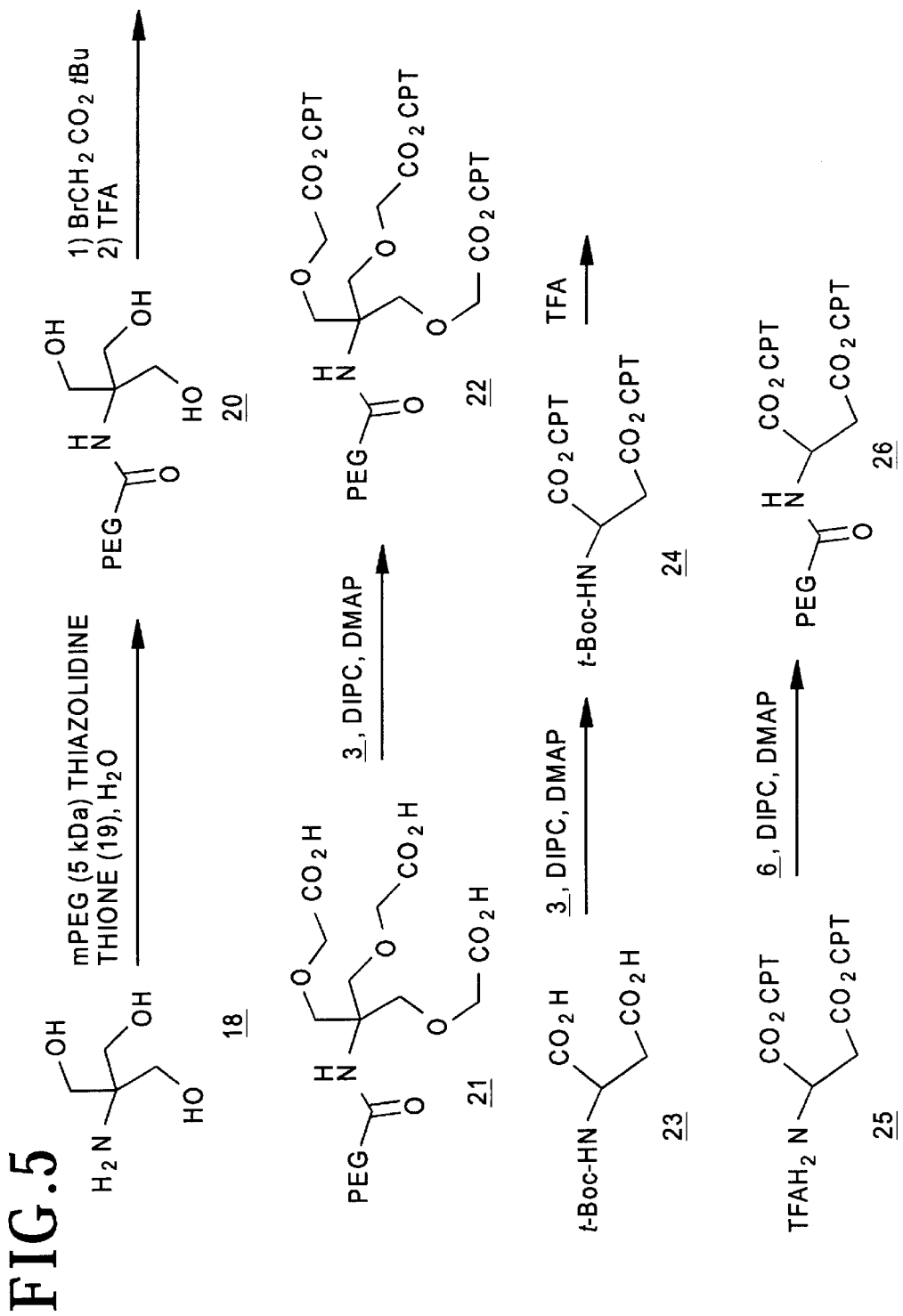

The prodrugs of the present invention can be prepared in at least two fashions which are schematically shown in FIGS. 1–2. Turning now to FIG. 1, Method A is described. The branched amine-containing group is provided in a protected form (IX), the protecting group is removed and the resulting unprotected amine terminal group (IXa) is reacted with an activated polymer of Formula (X)

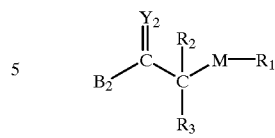

wherein M and $R_{1-3}$ are as defined above, $Y_2$ is O or S and $B_2$ is a leaving group which is capable of reacting with an unprotected amine, such as an activated carbonate moiety like para nitrophenyl or succinimidyl carbonate; a thiazolidine thione or other art recognized activating group to form (IXb). In the final synthesis step, a biologically active moiety having an available OH group is reacted with (IXb) to form the polymeric transport form (IXc). All variables shown in the Method A schematic of FIG. 1 are the same as previously defined herein and $B_3$ is a cleavable or reversible protecting group. Suitable protecting groups useful for this purpose may be any of a variety of organic moieties known to those of ordinary skill in the art and include, without limitation, t-Boc (tert-butyloxycarbonyl), Cbz (carbobenzyloxy) and TROC (trichloroethoxycarbonyl).

Deprotection is achieved by treatment of (IX) with a strong acid such as trifluoroacetic acid (TFA) or other haloacetic acid, HCl, sulfuric acid, etc., or by using catalytic hydrogenation HCl. Attachment of the B moiety, e.g. Drug-OH is preferably carried out in the presence of a coupling agent. A non-limiting list of suitable coupling agents include 1,3-diisopropylcarbodiimide (DIPC), any suitable dialkyl carbodiimides, 2-halo-1-alkyl-pyridinium halides, (Mukaiyama reagents), 1-(3-dimethylaminopropyl)-3-ethyl carbodiimide (EDC), propane phosphonic acid cyclic anhydride (PPACA) and phenyl dichlorophosphates, etc. which are available, for example from commercial sources such as Sigma-Aldrich Chemical, or synthesized using known techniques.

Preferably the substituents are reacted in an inert solvent such as methylene chloride, chloroform, toluene, DMF or mixtures thereof. The reaction also preferably is conducted in the presence of a base, such as dimethylaminopyridine, diisopropylethylamine, pyridine, triethylamine, etc. to neutralize any acids generated and at a temperature from 0° C. up to about 22° C. (room temperature).

Turning now to Method B illustrated in FIG. 2, an alternative synthetic technique is shown. In this embodiment, the protected intermediate (IX) is reacted with a B moiety, e.g. Drug-OH, prior to being deprotected. This results in the formation of a linkable amine-containing moiety (XI) which is then subjected to the deprotecting and polymer conjugating steps described above in Method A to form the polymer transport form (IXc).

In the case of the compounds corresponding to Formula (III), Methods A and B can be followed using a compound corresponding to Formula (XI) in place of (IX)

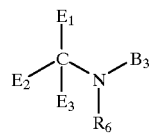

where $E_{1-3}$ and R6 are the same as that set forth above in Formula (III) and $B_3$ is a protecting group as defined above with regard to Methods A and B.

Regardless of the synthesis selected, some of the preferred compounds which result from the synthesis techniques described herein include (I'):

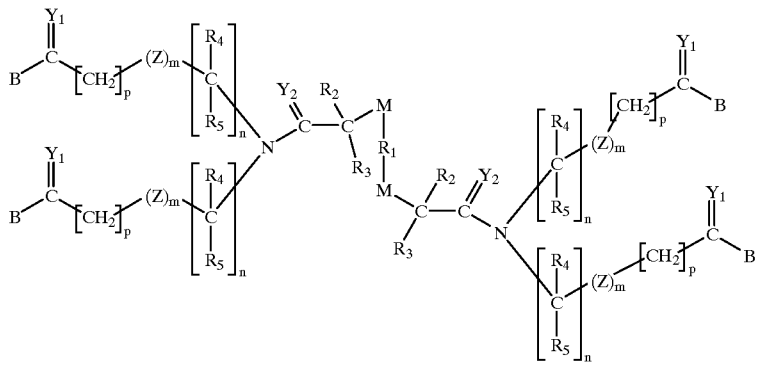

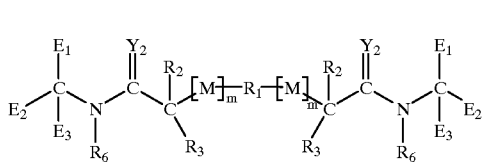

(VIII)

Additional compounds are illustrated below. CPT (camptothecin) has been used for illustrative purposes rather than for the purpose of limitation. In each case below, the portion of the compound shown as "CPTO$_2$C" is shown to illustrate that the biologically active moiety CPT attached to the polymeric transport system is actually a residue which results when the 20—OH undergoes a substitution reaction with the activated form of the transport system polymer.

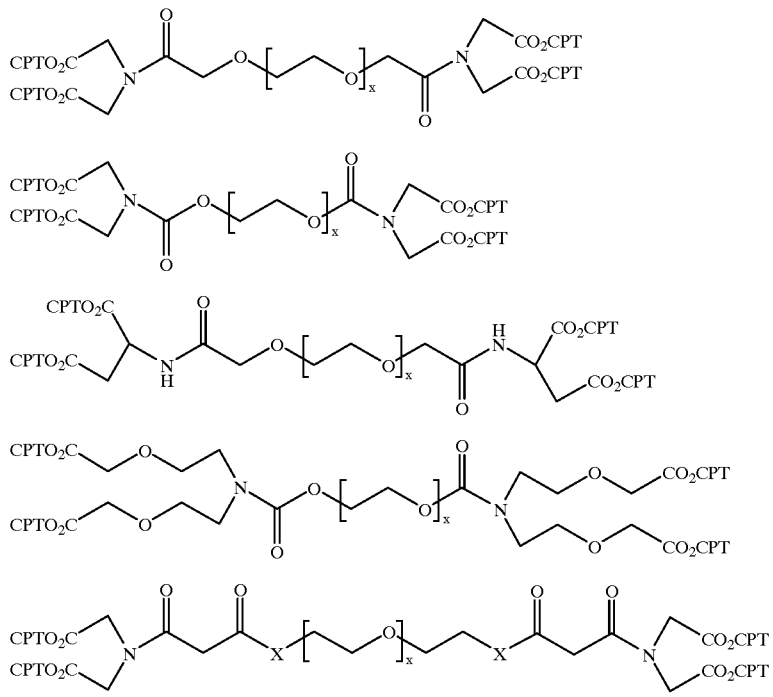

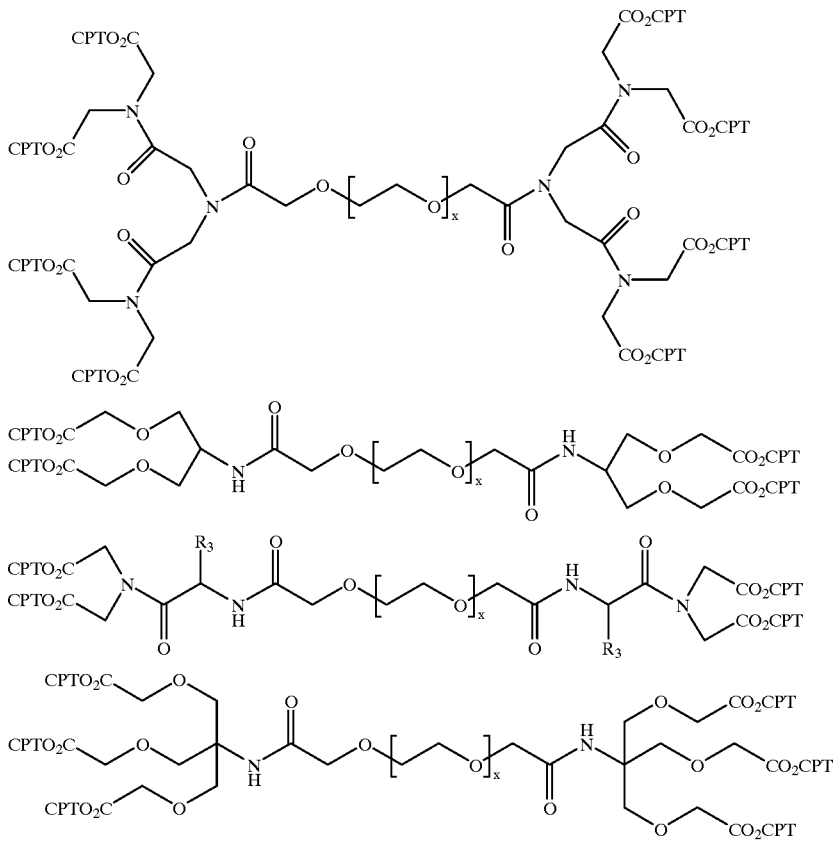

G. Methods Of Treatment

Another aspect of the present invention provides methods of treatment for various medical conditions in mammals. The methods include administering to the mammal in need of such treatment, an effective amount of a pro drug, such as a camptothecin-20-PEG ester, which has been prepared as described herein. The compositions are useful for, among other things, treating neoplastic disease, reducing tumor burden, preventing metastasis of neoplasms and preventing recurrences of tumor/neoplastic growths in mammals.

The amount of the prodrug administered will depend upon the parent molecule included therein. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. In general, however, prodrug taxanes are administered in amounts ranging from about 5 to about 500 mg/m$^2$ per day, based on the amount of the taxane moiety. Camptothecin and podophyllotoxin prodrugs are also administered in amounts ranging from about 5 to about 500 mg/m$^2$ per day. The range set forth above is illustrative and those skilled in the art will determine the optimal dosing of the prodrug selected based on clinical experience and the treatment indication. Actual dosages will be apparent to the artisan without undue experimentation.

The prodrugs of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may also be by infusion into a body space or cavity, as well as by inhalation and/or intranasal routes. In preferred aspects of the invention, however, the prodrugs are parenterally administered to mammals in need thereof

H. Examples

The following examples serve to provide further appreciation of the invention but are not meant in any way to restrict the effective scope of the invention. The underlined and bold-faced numbers recited in the Examples correspond to those shown in the Figures.

Example 1

Compound 2: N-t-Boc-iminodiacetic Acid

A mixture of iminodiacetic acid (1, 2 g, 15.03 mmol), di-t-butyl dicarbonate (3.9 g, 18.0 mmol), and sodium hydroxide (0.721 g, 18.0 mmol) in water (50 mL) was stirred at room temperature for 18 hours. The reaction solution was washed with 20 mL of methylene chloride (CH$_2$Cl$_2$) followed by adjusting pH to 2.5 with 6 N HCl. The resulting mixture was extracted with ethyl acetate (2×300 mL) and the combined organic layer was dried over anhydrous magnesium sulfate (MgSO$_4$). The solvent was removed in vacuo to give 1.0 g (29%) of 2.

$^1$H NMR (270 MHz, DMSO-d$_6$)δ 1.36 (s, 9H), 3.88 (s, 2H), 3.92 (s, 2H), 13.69 (bs, 2H). $^{13}$C NMR (67.80 MHz, DMSO-d$_6$) δ 27.84, 49.12, 49.64, 79.59, 154.79, 171.20.

Example 2
Compound 4: Coupling of 2 with Camptothecin(3)

A mixture of 2 (200 mg, 0.86 mmol) and camptothecin (3, 777 mg, 2.2 mmol) in anhydrous $CH_2Cl_2$ (50 mL) was cooled in an ice bath for 30 minutes before adding 1,3-diisopropylcarbodiimide (DIPC, 324 mg, 2.4 mmol) and 4-dimethylaminopyridine (DMAP, 272 mg, 2.2 mmol). The reaction mixture was left in the ice bath overnight and was allowed to warm to room temperature slowly. The solution was filtered and washed with water (20 mL) and 1N HCl (20 mL). The organic layer was dried over anhydrous $MgSO_4$ and concentrated. The residue was purified by silica gel column chromatography (2.5% methanol in $CH_2Cl_2$) to give 432 mg (56%) of 4.

$^1$H NMR (270 MHz, $CDCl_3$) δ 1.00 (t, 6H, J=8.1 Hz), 1.20 (s, 3H), 1.22 (s, 3H), 1.38 (s, 3H), 1,44 (s, 3H), 2.17 (m, 4H), 4.01–4.36 (m, 4H), 5.26 (d, 2H, J=13.5 Hz), 5.38 (d, 2H, J=10.1 Hz), 5.41 (d, 2H, J=5.4 Hz), 5.24 (d, 2H, J=8.1 Hz), 7.25 (d, 2H, J=13.5 Hz), 7.37 (s, 2H), 7.62 (t, 2H, J=8.1 Hz), 7.79 (q, 2H, J=8.1 Hz), 7.90 (m, 2H), 8.19 (m, 2H), 8.35 (d, 2H, J=10.8 Hz). $^{13}$C NMR (67.80 MHz, $CDCl_3$) δ 7.59, 22.20, 23.37, 25.35, 28.07, 31.57, 31.75, 49.37, 49.56, 49.97, 64.38, 66.94, 74.94, 76.76, 76.79, 78.82, 81.74, 95.83, 96.69, 119.75, 120.12, 127.86, 128.04, 128.15, 128.36, 129.59, 130.40, 130.60, 130.87, 131.10, 145.65, 145.84, 146.31, 146.40, 148.86, 152.14, 152.30, 154.81, 157.34, 166.83, 167.25, 168.78, 169.07.

Example 3
Compound 5: Deprotection of 4

A solution of 4 (300 mg, 0.34 mmol) in anhydrous $CH_2Cl_2$ (5 mL) and trifluoroacetic acid (TFA, 2.5 mL) was stirred at room temperature for 3 hours. The reaction mixture was concentrated and the solid was recrystallized from ethyl ether to give 258 mg (78%) of 5 as a TFA salt.

$^1$H NMR (270 MHz, DMSO-$d_6$) δ 0.92 (t, 6H, J=8.1 Hz), 2.16 (q, 4H, J=8.1 Hz), 4.19 (d, 2H, J=16.2 Hz), 4.36 (d, 2H, J=16.2 Hz), 5.26 (s, 4H), 5.54 (s, 4H), 7.22 (s, 2H), 7.71 (t, 2H, J=8.1 Hz), 7.84 (t, 2H, J=8.1 Hz), 8.10 (s, 2H), 8.13 (s, 2H), 8.67 (s, 2H). $^{13}$C NMR (67.80 MHz, DMSO-$d_6$) δ 7.47, 30.08, 38.58, 38.88, 39.19, 39.50, 39.81, 40.12, 40.42, 46.81, 50.19, 66.32, 77.37, 95.13, 118.79, 127.71, 127.92, 128.54, 128.68, 129.69, 130.45, 131.62, 144.65, 146.03, 147.80, 152.21, 156.41, 166.76.

Example 4
Compound 7: Pegylation of 5

PEG (40 kDa) dicarboxylic acid (6, 2.0 g, 0.05 mmol) was azeotroped for 2 hours in toluene, followed by removal of the solvent in vacuo. Anhydrous $CH_2Cl_2$ (20 mL) was added to the residue followed by the addition of 5 (0.16 g, 0.20 mmol), DIPC (25 mg, 0.20 mmol), and DMAP (25 mg, 0.20 mmol). The reaction mixture was stirred at room temperature overnight followed by removal of the solvent in vacuo. The residue was recrystallized from 2-propanol to yield 0.8 g (69%) of 7 as a white solid.

$^{13}$C NMR (67.80 MHz, $CDCl_3$) δ 7.25, 31.43, 49.35, 49.64, 66.80, 68.66–71.16 (PEG), 76.06, 95.57, 119.96, 127.71, 127.89, 128.13, 129.38, 130.34, 130.89, 145.11, 146.09, 148.54, 151.93, 156.94, 166.89, 170.58.

Example 5
Compound 9: Coupling of 1 with PEG (40 kDa) Dithiazolidine Thione (8)

PEG (40 kDa) dithiazolidine thione (8, 1 g, 0.025 mmol) is added to the mixture of 1 (14 mg, 0.11 mmol) and N,N-diisopropylethylamine (DIPEA, 37 μL, 0.20 mmol) in anhydrous $CH_2Cl_2$ (15 mL). The mixture is stirred at room temperature overnight. The solvent is removed under reduced pressure and the residue is recrystallized from 2-propanol to give 9.

Example 6
Compound 7 from Compound 9

DIPC (13 mg, 0.10 mmol) is added to the mixture of 9 (1.0 g, 0.025 mmol), DMAP (13 mg, 0.10 mmol), and 3 (35 mg, 0.1 mmol) in anhydrous $CH_2Cl_2$ (20 mL). The solution is stirred at room temperature overnight followed by removal of the solvent in vacuo. The residue is recrystallized from 2-propanol (80 mL) to give 7.

Example 7
Compound 11: N-t-Boc-diethanolamine

A solution of di-t-butyl dicarbonate (26.46 g, 0.12 mol) in chloroform (50 mL) was added to the solution of diethanolamine (10, 12.63 g, 0.12 mol) in chloroform (50 mL) slowly at room temperature. The reaction solution was stirred at room temperature for 1 hour, followed by washing with water (30 mL) and the organic layer was dried over anhydrous $MgSO_4$. The solvent was removed under reduced pressure to give 11 (20 g, 83%).

$^1$H NMR (270 MHz, $CDCl_3$) δ 1.46 (s, 9H), 3.41 (bs, 4H), 3.76 (bs, 4H), 4.69 (bs, 2H). $^{13}$C NMR (67.80 MHz, $CDCl_3$) δ 28.30, 52.22, 61.63, 80.13, 156.22.

Example 8
Compound 12

Compound 11 (9.5 g, 46.34 mmol) was dissolved in anhydrous toluene (200 mL) by warming and the solution was cooled to −20° C., followed by the addition of potassium t-butoxide (1M solution in t-butanol, 70 mL, 70 mmol). The mixture was stirred at −20° C. for 5 hours and was cooled to −30° C. Ethyl bromoacetate (30.96 g, 185.35 mmol) was added to the solution and the reaction mixture was stirred at −15° C. for 3 hours. The solution was washed with water (50 mL) and the organic layer was dried over anhydrous $MgSO_4$. The solvent was removed in vacuo to give a crude product which was purified by silica gel column chromatography (ethyl acetate/hexane=1:1, v/v) to give 8.2 g (48%) of 12.

$^1$H NMR (270 MHz, $CDCl_3$) δ 1.28 (t, 6H, J=5.4 Hz), 1.45 (s, 9H), 3.51 (bs, 4H), 3.67 (bs, 4H), 4.08 (s, 4H), 4.21 (q, 4H, J=5.4 Hz). $^{13}$C NMR (67.80 MHz, $CDCl_3$) δ 13.95, 28.15, 47.61, 60.49, 68.16, 69.96, 79.42, 155.14, 170.02.

Example 9
Compound 13

A solution of NaOH (10 g, 250 mmol) in water (10 mL) and ethanol (100 mL) was added to a solution of 12 (8.0 g, 21.22 mmol) in ethanol (80 mL). The reaction solution was stirred at room temperature for 1.5 hours and cooled to 0° C. The pH was adjusted to 2.5 with 6N HCl. The mixture was filtered and the filtrate was concentrated in vacuo. Chloroform (300 mL) was added to the residue and washed with water (3×50 mL). The organic layer was dried over anhydrous $MgSO_4$ and concentrated under reduced pressure to give 5.0 g (73%) of 13.

$^1$H NMR (270 MHz, $CDCl_3$) δ 1.45 (s, 9H), 3.51 (bs, 4H), 3.71 (bs, 4H), 4.13 (s, 4H), 9.35 (bs, 2H). $^{13}$C NMR (67.80 MHz, $CDCl_3$) δ 28.35, 48.13, 67.97, 70.24, 80.54, 155.93, 173.95.

Example 10
Compound 14: Coupling of 13 with 3

A mixture of 13 (2 g, 6.23 mmol), 3 (5.643 g, 16.20 mmol), DMAP (1.979 g, 16.20 mmol), and DIPC (2.041 g, 16.20 mmol) in anhydrous CH$_2$Cl$_2$ (50 mL) was stirred at room temperature for 20 hours. The reaction mixture was filtered and the filtrate was washed with water (30 mL) and dried over anhydrous MgSO$_4$. The solution was concentrated to give a crude product as a solid which was purified by silica gel column chromatography (2.5% methanol in CH$_2$Cl$_2$) to give 14 as a light yellow solid (2.45 g, 40%).

$^1$H NMR (270 MHz, CDCl$_3$) δ 0.96 (t, 6H, J=8.1 Hz), 1.38 (s, 9H), 2.20 (qd, 4H, J=13.5, 8.1 Hz), 3.47 (bs, 4H), 3.63 (bs, 4H), 4.25 (s, 4H), 5.24 (s, 4H), 5.39 (d, 2H, J=13.5 Hz), 5.66 (d, 2H, J=13.5 Hz), 7.19 (s, 2H), 7.65 (t, 2H, J=6.8 Hz), 7.80 (t, 2H, J=6.8 Hz), 7.93 (d, 2H, J=8.1 Hz), 8.2 (d, 2H, J=8.1 Hz), 8.36 (s, 2H). $^{13}$C NMR (67.80 MHz, CDCl$_3$) δ 7.46, 28.27, 31.70, 47.53, 47.74, 49.83, 67.06, 67.84, 70.37, 76.22, 79.68, 95.76, 120.19, 127.92, 128.07, 128.36, 129.53, 130.55, 131.07, 145.29, 146.30, 148.71, 152.15, 155.25, 157.18, 167.09, 169.36.

Example 11
Compound 15: Deprotection of 14

Compound 14 (0.74 g, 0.75 mmol) was dissolved in CH$_2$Cl$_2$ (10 ML) and TFA (5 mL). The reaction solution was stirred at room temperature for 2 hours and concentrated under reduced pressure. The residue was recrystallized from CH$_2$Cl$_2$-ethyl ether to give 0.6 g (100%) of 15 as a TFA salt.

$^1$H NMR (270 MHz, CDCl$_3$) δ 0.9, 2.1, 3.3, 3.9, 4.4, 5.2, 5.4, 5.6, 7.2, 7.6, 7.8, 7.9, 8.1, 8.4. $^{13}$C NMR (67.80 MHz, CDCl$_3$) δ 7.17, 31.20, 46.85, 49.77, 53.40, 66.43, 67.61, 76.79, 95.46, 119.51, 127.70, 127.94, 128.43, 129.04, 130.36, 131.05, 145.00, 146.23, 148.29, 151.86, 156.87, 166.85, 169.49.

Example 12
Compound 16: Coupling of 15 with Di-SC-PEG (40 kDa)

A mixture of 15 (79,8 mg, 0,09 mmol), di-SC-PEG (40 kDa, 1.0 g, 0.025 mmol), and DMAP (11.1 mg, 0.09 mmol) in anhydrous chloroform (20 mL) was stirred at room temperature overnight. The solvent was removed in vacuo and the residue was recrystallized from 2-propanol (80 mL) to give 0.92 g (92%) of 16.

$^{13}$C NMR(67.80 MHz, CDCl$_3$) δ 7.15, 31.54, 47.68, 49.63, 64.17, 66.73, 67.92, 69.13–71.28 (PEG), 76.16, 95.33, 120.01, 127.57, 127.83, 127.97, 128.39, 129.45, 130.15, 130.71, 145.28, 146.22, 148.70, 152.12, 155.74, 156.94, 166.52, 168.90.

Example 13
Compound 17: Coupling of 15 with PEG (40 kDa) Dicarboxylic Acid (6)

Compound 6 (3 g, 0.075 mmol) was azeotroped for 2 hours in 90 mL of toluene. The solvent was removed in vacuo and the residue was dissolved in 50 mL of anhydrous CH$_2$Cl$_2$. Compound 15 (263.5 mg, 0.3 mmol), DMAP (45.7 mg, 0.38 mmol), and DIPC (37.7 mg, 0.30 mmol) were added to the solution and the reaction mixture was stirred at room temperature overnight. The reaction solution was diluted with 100 mL of CH$_2$Cl$_2$ and washed with 1N HCl (2×20 mL) and water (20 mL). The organic layer was dried over anhydrous MgSO$_4$ and the solvent was removed under reduced pressure. The residue was recrystallized from 2-propanol (100 mL) to give 2.44 g (80%) of 17.

$^1$H NMR (270 MHz, CDCl$_3$) δ 1.01, 2.2, 2.9, 3.2–3.9 (PEG), 4.2, 5.2, 5.3, 5.7, 7.15, 7.65, 7.8, 7.95, 8.2, 8.5. $^{13}$C NMR (67.80 MHz, CDCl$_3$) δ 6.91, 31.01, 45.05, 47.50, 49.33, 66.36, 67.21, 67.30–71.16 (PEG), 75.62, 75.72, 77.92, 94.86, 119.31, 119.38, 127.31, 127.53, 127.63, 127.99, 128.85, 129.93, 130.74, 144.61, 145.83, 148.05, 151.54, 156.45, 166.34, 168.47, 168.55, 169.23.

Example 14
Compound 20: Coupling of TRIS (18) with MPEG (20 kDa) Thiazolidine Thione (19)

mPEG (20 kDa) thiazolidine thione (19, 4 g, 0.2 mmol) was added to a solution of tris(hydroxymethyl) aminomethane (TRIS, 18, 2.4 g, 20 mmol) in water (60 mL). The mixture was stirred at room temperature overnight, followed by extraction with CH$_2$Cl$_2$ (2×50 mL). The combined organic layer was washed with brine (60 mL) and dried over anhydrous MgSO$_4$. The solvent was removed under reduced pressure and the residue was recrystallized from 2-propanol to give 2.0 g (50%) of 20.

$^{13}$C NMR (67.80 MHz, CDCl$_3$) δ 58.33, 60.99, 62.31, 69.91–71.28 (PEG), 170.51.

Example 15
Compound 21

A solution of 20 (10 g, 2 mmol) in 100 mL of toluene is azeotroped for 2 hours and was cooled to 35° C., followed by the addition of 10.5 mL (10.5 mmol) of 1.0 M potassium t-butoxide in t-butanol. The mixture is stirred for 1 h at 35° C., followed by the addition of 3.9 g (20 mmol) of t-butyl bromoacetate. The reaction mixture is stirred at 40° C. overnight. The mixture is filtered through celite and the solvent was removed in vacuo. The residue is recrystallized from chilled CH$_2$Cl$_2$-ethyl ether to yield ester of 20. The ester is dissolved in CH$_2$Cl$_2$ (100 mL) and TFA (50 mL). The reaction solution is stirred at room temperature for 2 hours and concentrated under reduced pressure. The residue is recrystallized from CH$_2$Cl$_2$-ethyl ether to give 21.

Example 16
Compound 22: Coupling of 3 with 21

Compound 21 (3 g, 0.56 mmol) is azeotroped for 2 hours in 90 mL of toluene. The solvent is removed in vacuo and the residue is dissolved in 60 mL of anhydrous CH$_2$Cl$_2$. Compound 3 (1.17 g, 3.4 mmol), DMAP (829.6 mg, 6.8 mmol), and DIPC (1.37 g, 13.6 mmol) are added to the solution and the reaction mixture is stirred at room temperature overnight. The reaction solution is diluted with 100 mL of CH$_2$Cl$_2$ and washed with 1N HCl (2×20 mL) and water (20 ML). The organic layer is dried over anhydrous MgSO$_4$ and the solvent is removed under reduced pressure. The residue is recrystallized from 2-propanol (300 ML) to give 22.

Example 17
Compound 24: Coupling of 3 with N-t-Boc-L-Aspartic Acid (23)

DIPC (0.72 g, 5.8 mmol) was added to a solution of N-t-Boc-L-aspartic acid (23, 1.34 g, 5.8 mmol), 3 (2.0 g, 5.8 mmol), DMAP (0.7 g, 5.8 mmol), and in anhydrous CH$_2$Cl$_2$ (25 mL) at 0° C. The mixture was allowed to warm to room temperature overnight, followed by washing with 1% aqueous sodium bicarbonate (4×15 mL) and 0.1 N HCl (2×15 mL). The organic layer was dried over anhydrous MgSO$_4$. The solution was concentrated to give a crude product as a solid which was recrystallized in methanol to give 24 (2.1 g, 40%).

$^{13}$C NMR (67.80 MHz, CDCl$_3$) δ 7.25, 7.47, 27.20, 27.83, 28.12, 31.30, 31.48, 35.66, 49.74, 66.46, 66.83, 80.11, 96.25, 96.57, 119.64, 119.86, 127.79, 127.91, 128.17, 128.36, 129.48, 129.59, 130.40, 130.92, 145.20, 145.84, 146.05, 148.59, 151.89, 152.07, 155.18, 156.84, 156.92, 166.51, 167.22, 169.68, 169.90.

Example 18
Compound 25: Deprotection of 24

A solution of 24 (500 mg, 0.56 mmol) in anhydrous $CH_2Cl_2$ (5 mL) and trifluoroacetic acid (TFA, 2.5 mL) was stirred at room temperature for 1 hour, followed by addition of ethyl ether (40 mL). The solid was filtered and washed with ethyl ether to give 25 (0.4 g, 75%).

Example 19
Compound 26: Coupling of 25 with 6

PEG (40 kDa) dicarboxylic acid (6, 1.0 g, 0.025 mmol) was azeotroped for 2 h in toluene, followed by removal of the solvent in vacuo. Anhydrous $CH_2Cl_2$ (20 mL) was added to the residue followed by the addition of 25 (94 mg, 0.10 mmol), DIPC (13 mg, 0.10 mmol), and DMAP (25 mg, 0.20 mmol). The reaction mixture was stirred at room temperature overnight followed by removal of the solvent in vacuo. The residue was recrystallized from 2-propanol to yield 0.81 g (81%) of 26 as a white solid.

The various publications, patents, patent applications and published applications mentioned in this application are hereby incorporated by reference herein.

While there have been described what are presently believed to be the preferred embodiments of the invention, those skilled in the art will realize that changes and modifications may be made without departing from the spirit of the invention. It is intended to claim all such changes and modifications as fall within the true scope of the invention.

We claim:

1. A compound comprising the formula:

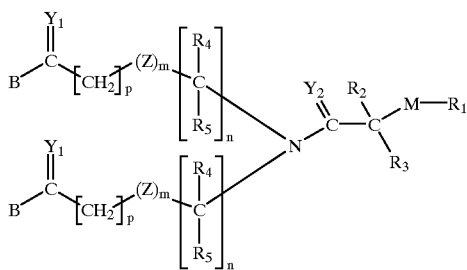

(I)

wherein:

B is a leaving group, OH, a residue of a hydroxyl-containing moiety or

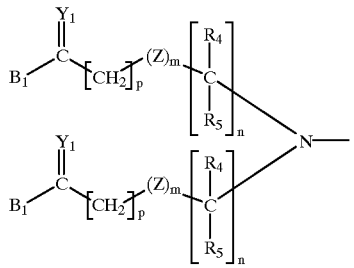

wherein $B_1$ is a leaving group, OH or a hydroxyl-containing moiety;

$Y_{1-2}$ are independently O or S;

M is either X or Q; wherein X is an electron withdrawing group and Q is a moiety containing a free electron pair positioned three to six atoms from $C(=Y_2)$;

$R_{2-5}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;

(m) is zero or one;

(n) is a positive integer;

(p) is zero or a positive integer;

Z is an electron withdrawing group; and $R_1$ is a polymeric residue.

2. The compound of claim 1, wherein $R_1$ further comprises a capping group A, which is selected from the group consisting of hydrogen, $CO_2H$, $C_{1-6}$ alkyl moieties, dialkyl acyl urea alkyls and

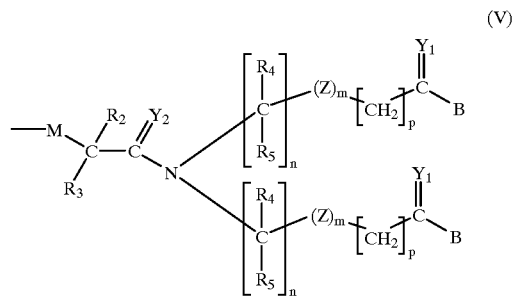

(V)

wherein

B, M, $R_{2-5}$, $Y_{1-2}$, Z, m, n, and p are the same as that set forth in claim 1.

3. The compound of claim 1, wherein $Y_1$ and $Y_2$ are oxygen.

4. The compound of claim 1, wherein $R_{2-5}$ are hydrogen.

5. The compound of claim 1, wherein X is selected from the group consisting of O, S, SO, $SO_2$ and $NR_{6a}$, wherein $R_{6a}$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls.

6. The compound of claim 1, wherein (p) is 1.

7. The compound of claim 1, wherein $R_1$ comprises a polyalkylene oxide residue.

8. The compound of claim 7, wherein said polyalkylene oxide residue comprises polyethylene glycol.

9. The compound of claim 8, wherein (n) is 1 or 2.

10. The compound of claim 1, wherein (m) is 1.

11. The compound of claim 1, wherein said polymeric residue has a molecular weight of from about 2,000 to about 100,000.

12. The compound of claim 11, wherein said polymeric residue has a molecular weight of from about 20,000 to about 40,000.

13. The compound of claim 1, wherein B is a residue of a member of the group consisting of camptothecin, camptothecin analogs, paclitaxel, taxoteres, gemcitabine, podophyllotoxin, fluconazole, ciclopirox, amphoteracin B, nystatin, triazoles, papulocandins, pneumocandins, echinocandins, polyoxins, nikkomycins, pradimicins, benanomicins, forskolin, combretastatin, vinblastine, doxorubicin, AraC, maytansine, vancomycin and erythromycin.

14. A compound of claim 2, having the formula:

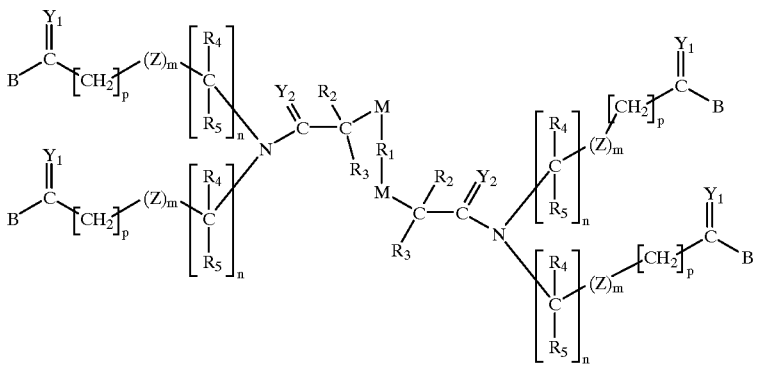

15. A method of preparing a polymeric transport system, comprising
a) reacting a compound of Formula (IXa)

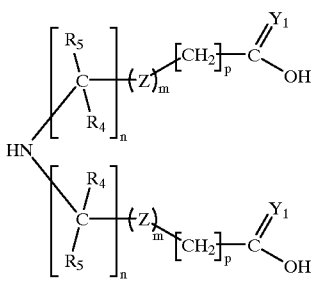
(IXa)

with a compound of Formula (X)

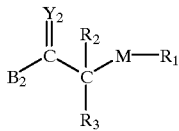
(X)

wherein:

$Y_{1-2}$ are independently O or S;

M is selected from either X or Q; wherein X is an electron withdrawing group and Q is a moiety containing a free electron pair positioned three to six atoms from $C(=Y_2)$;

$R_{2-5}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;

(m) is zero or one;

(n) is a positive integer;

(p) is zero or a positive integer;

Z is an electron withdrawing group;

$B_2$ is a leaving group;

$R_1$ is a polymeric residue; and b) reacting the resultant compound with a sufficient amount of a biologically active moiety having an OH group.

16. A method of preparing a polymeric transport system, comprising a) reacting a compound of Formula (IX)

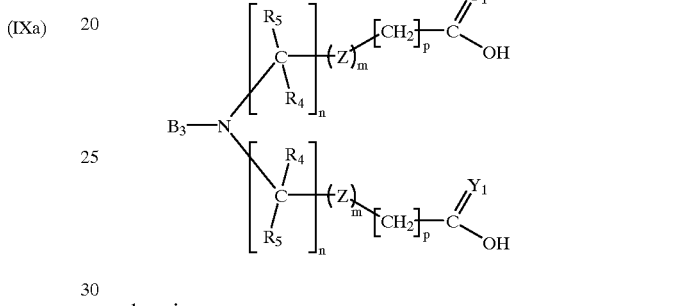
(IX)

wherein:

$B_3$ is a cleavable protecting group;

$Y_1$ is O or S;

$R_{4-5}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;

(m) is zero or one;

(n) is a positive integer;

(p) is zero or a positive integer; and

Z is an electron withdrawing group with a biologically active moiety having an OH group b) deprotecting the resultant intermediate by removing $B_3$; and c) reacting the deprotected intermediate compound with a compound of Formula (X)

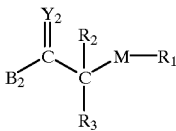
(X)

wherein:

$B_2$ is a leaving group;

$Y_2$ is O or S;

M is selected from either X or Q; wherein X is an electron withdrawing group and Q is a moiety containing a free electron pair positioned three to six atoms from $C(=Y_2)$;

$R_{2-3}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls; and $R_1$ is a polymeric residue.

17. A compound of claim 14, having the formula selected from the group consisting of:

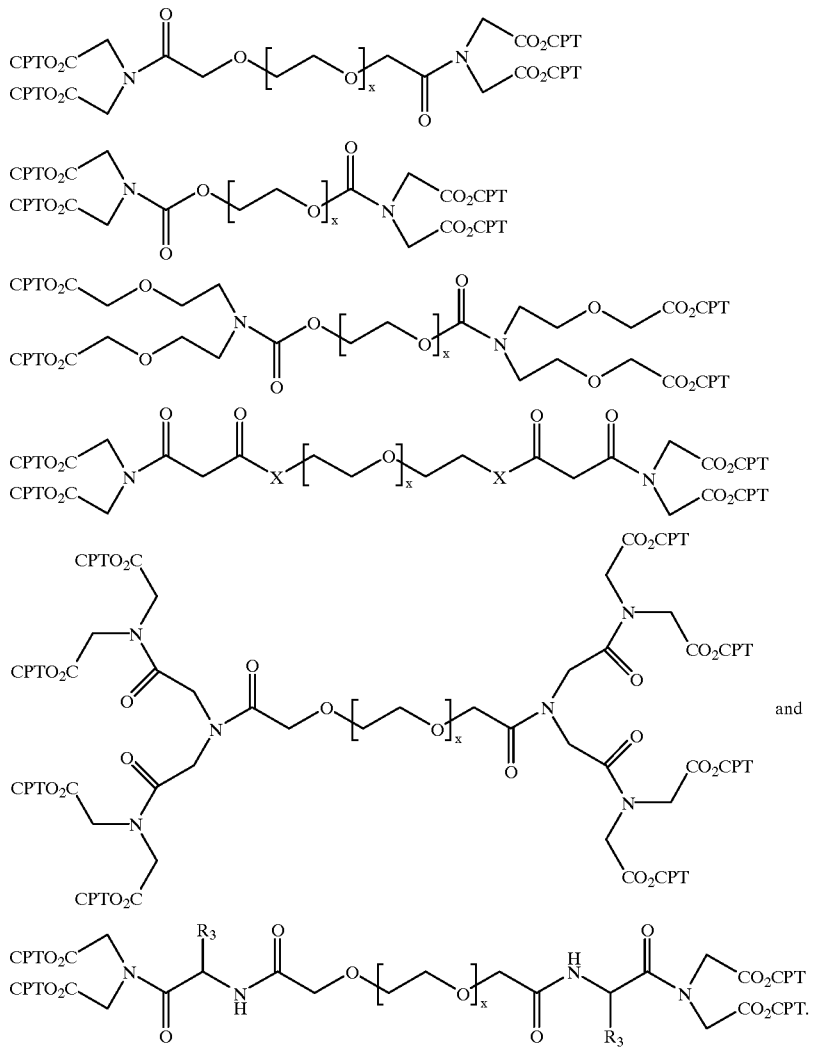
Wherein CPT represents the residue of a biologically active compound which remains after said biologically active compound has attached to the polymeric carrier.
* * * * *